US00PP16845P3

(12) United States Plant Patent
Zaiger et al.

(10) Patent No.: US PP16,845 P3
(45) Date of Patent: Jul. 18, 2006

(54) PEACH TREE NAMED 'VISTA SNOW'

(50) Latin Name: *Prunus persica*
Varietal Denomination: Vista Snow

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/820,946

(22) Filed: Apr. 9, 2004

(65) Prior Publication Data

US 2005/0229278 P1 Oct. 13, 2005

(51) Int. Cl.
*A01H 5/00* (2006.01)

(52) U.S. Cl. ..... Plt./195

(58) Field of Classification Search ..... Plt./195
See application file for complete search history.

*Primary Examiner*—Kent Bell
*Assistant Examiner*—June Hwu

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit ripening during the early maturing season.
2. Having a low winter chilling requirement of approximately 250 hours at or below 45° F.
3. Fruit with a mild, sweet, sub-acid flavor.
4. Vigorous, upright tree growth.
5. Heavy and regular production of fruit.
6. Fruit with a high degree of attractive orange-red skin color.

1 Drawing Sheet

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of peach tree was originated and asexually reproduced by us in our experimental orchard located near Modesto, Calif.

PRIOR VARIETIES

Among the existing varieties of peach and nectarine trees, which are known to us, and mentioned herein, 'Desertgold' Peach (non-patented), 'Floraprince' Peach (non-patented), 'Rich May' Peach (U.S. Plant Pat. No. 7,432), 'Redwing' Peach (U.S. Plant Pat. No. 621), 'Giant Babcock' Peach (U.S. Plant Pat. No. 1,353), 'White Lady' Peach (U.S. Plant Pat. No. 5,821), 'May Crest' Peach (U.S. Plant Pat. No. 4,064) and 'Early Sungrand' Nectarine (U.S. Plant Pat. No. 1,420).

ORIGIN OF THE VARIETY

The new and distinct variety of peach tree (*Prunus persica*) was originated by us in our experimental orchard located near Modesto, Calif. as a first generation cross between two proprietary seedlings with field identification numbers '174LE309' and '2LD470'. The maternal parent (174LE309) was originated by us from crosses between the following varieties; 'Desertgold' Peach (non-patented), 'Floraprince' Peach (non-patented), 'Rich May' Peach (U.S. Plant Pat. No. 7,432) and 'Early Sungrand' Nectarine (U.S. Plant Pat. No. 1,420). The pollen parent (2LD470) originated from crosses between the following varieties; 'Redwing' Peach (U.S. Plant Pat. No. 621), 'Giant Babcock' Peach (U.S. Plant Pat. No. 1,353), 'White Lady' Peach (U.S. Plant Pat. No. 5,821), 'May Crest' Peach (U.S. Plant Pat. No. 4,064) and 'Early Sungrand' Nectarine (U.S. Plant Pat. No. 1,420). We planted and maintained a large group of these first generation seedlings on their own root system, during which time one seedling, which is the present variety, exhibited desirable tree and fruit characteristics and was selected in 1998 for asexual propagation and commercialization.

ASEXUAL REPRODUCTION OF THE VARIETY

Asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree is of large size, vigorous, upright growth and a regular and productive bearer of medium size, firm, white flesh, clingstone fruit with a mild, sweet, sub-acid flavor and excellent eating quality. The fruit is further characterized by ripening in the early maturity season, being relatively uniform in ripening, having cream skin color, nearly overspread with an attractive orange-red blush and nearly globose in shape. The tree having a low winter chilling requirement of approximately 250 hours at or below 45° F. and, in comparison to the low chilling variety 'Desertgold' Peach (non-patented), the fruit of the new variety is white flesh instead of yellow, has firmer flesh with greater storage and shipping quality, and is approximately 27 days earlier in maturity. In comparison to the yellow flesh peach 'May Crest' Peach (U.S. Plant Pat. No. 4,064), the new variety requires approximately 400 hours less winter chilling, has white flesh and is approximately 17 days earlier in maturity. In comparison to its maternal plant (174LE309) the fruit of the new variety has white flesh instead of yellow and matures approximately 5 days earlier. In comparison to the paternal parent (2LD470), the tree of the new variety requires approximately 150 hours less winter chilling and produces fruit that are larger in size with improved flavor.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of 5 year old specimens grown near Modesto, Calif., with color in accordance with Munsell Book of Color.

Tree:

*Size.*—Large, normal for peach trees. Pruned 3 to 3.5 meters in height for economical harvesting of fruit.

*Vigor.*—Vigorous, tree growth of 1.5 to 2 meters the first growing season. Varies with fertility and type of the soil.

*Form.*—Upright. Usually pruned to vase shape.

*Branching habit.*—Upright, crotch angle approximately 35°, increases with heavy crop load.

*Productivity.*—Productive, normal thinning and spacing of fruit necessary for desired market size fruit.

*Bearer.*—Regular, adequate fruit set 3 consecutive years. No alternate bearing observed.

*Fertility.*—Self fertile.

*Density.*—Medium dense. Pruning to vase shape desirable to enhance fruit color and keep fruit wood healthy.

*Hardiness.*—Hardy in all stone fruit growing areas of California. Tree grown in USDA Hardiness Zone 9. Winter chilling requirement approximately 250 hours at or below 45° F.

Trunk:

*Size.*—Medium stocky. Average circumference 49.0 cm at 20.8 cm above ground on a 5 year old tree.

*Stocky.*—Medium stocky.

*Texture.*—Medium shaggy.

*Color.*—Varies from 5YR 6/2 to 5YR 5/2.

Branches:

*Size.*—Medium, normal for peach trees. Average circumference 25.1 cm at 1 meter above ground. Average crotch angle 35°.

*Surface texture.*—New growth smooth, varies from medium to rough with age.

*Lenticels.*—Average number 54 in a 25.8 square cm area. Average length 2.9 mm. Average width 1.1 mm. Color varies from 5YR 6/8 to 5YR 5/8.

*Color.*—New growth varies from 5GY 6/6 to 7.5R 5/4 when exposed to sunlight. Old growth varies from 5YR 4/4 to 7.5YR 3/4. Varies with age of growth.

Leaves:

*Size.*—Large. Average length 146.5 mm. Average width 33.0 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 10.7 mm. Average width 1.5 mm. Color varies from 2.5GY 6/6 to 5GY 7/6. Grooved longitudinally. Glabrous.

*Glands.*—Reniform. Size — medium. Average length 1.2 mm. Average diameter 0.7 mm. Average number 3, varies from 3 to 5. Located primarily on base of leaf blade and upper portion of petiole. Color varies from 2.5GY 7/6 to 2.5GY 6/8.

*Color.*—Upper surface varies from 2.5GY 4/6 to 5GY 3/6. Lower surface varies from 5GY 5/4 to 5GY 4/4. Midvein color varies from 2.5GY 7/6 to 5GY 7/6.

Flower buds:

*Size.*—Large. Average length 14.6 mm. Average diameter 9.9 mm.

*Hardiness.*—Hardy in all stone fruit growing areas of California.

*Form.*—Plump, conical, becoming elongated before opening.

*Pedicel.*—Average length 3.5 mm. Average width 1.4 mm. Color varies from 2.5GY 6/8 to 5GY 5/6.

*Color.*—Varies from 7.5RP 5/4 to 5RP 8/6.

Flowers:

*Size.*—Large, showy. Average height 18.5 mm. Average diameter 36.2 mm.

*Petals.*—Number 5, alternately arranged to sepals. Orbicular, apex rounded, base narrows at point of attachment. Average length 17.1 mm. Average width 16.0 mm. Margin — sinuate, slightly cupped. Upper and lower surfaces glabrous. Color varies from 5RP 8/6 to 7.5RP 8/6.

*Sepals.*—Number 5, alternately arranged to petals. Shape — ovate, apex rounded. Average length 5.6 mm. Average width 4.7 mm. Upper surface glabrous, lower surface pubescent. Color — upper surface varies from 5GY 6/6 to 5GY 5/8, lower surface varies from 7.5RP 4/4 to 7.5RP 3/6. Margin — entire.

*Stamens.*—Average number 44 per flower. Average filament length 14.0 mm. Filament color varies from N9.5/ to 5RP 8/4. Anther color varies from 10RP 5/10 to 10RP 4/10.

*Pollen.*—Self fertile. Color — 2.5Y 8/10.

*Pistil.*—Number — normally one, varies from 1 to 2. Surface pubescent. Average length 15.7 mm. Position of stigma — average 1.1 mm above anthers. Color varies from 10Y 8/4 to 10Y 8/6.

*Fragrance.*—Slight.

*Blooming period.*—Date of First Bloom Feb. 17, 2003. Date of Petal Fall Feb. 27, 2003. Varies slightly with climatic conditions.

*Color.*—Varies from 5RP 7/6 to 7.5RP 8/4, color fades with age of flower.

*Number flowers per flower bud.*—Normally one.

*Pedicel.*—Average length 3.9 mm. Average width 1.3 mm. Color varies from 2.5GY 6/6 to 5GY 5/6.

Fruit:

*Maturity when described.*—Firm ripe.

*Date of first picking.*—May 5, 2003.

*Date of last picking.*—May 10, 2003, varies slightly with climatic conditions.

*Size.*—Medium. Average diameter axially 56.6 mm. Average transversely in suture plane 57.2 mm. Average weight 103.5 grams. Average weight varies slightly with fertility of the soil, amount of thinning and climatic conditions.

*Form.*—Globose.

*Suture.*—Shallow, extends from base to apex.

*Ventral surface.*—Nearly smooth, very slightly lipped.

*Apex.*—Slight tip.

*Base.*—Retuse.

*Cavity.*—Rounded to slightly elongated in suture plane. Average depth 3.3 mm. Average diameter 10.2 mm.

Stem:

*Size.*—Small. Average length 7.2 mm. Average diameter 3.6 mm.

*Color.*—Varies from 2.5GY 6/8 to 5GY 6/6.

Flesh:

*Ripens.*—Evenly.

*Texture.*—Firm.

*Fibers.*—Few, small, tender.

*Firmness.*—Firmer than most early maturing varieties, such as 'Desertgold' Peach (non-patented).

*Aroma.*—Slight to moderate.

*Amydgalin.*—Undetected.

*Eating quality.*—Excellent, mild, sub-acid.

*Flavor.*—Very good.

*Juice.*—Moderate amount, enhances flavor.

*Brix.*—Average 11.1°, varies slightly with amount of fruit per tree and climatic conditions.

*Color.*—Varies from 5Y 9/2 to 7.5Y 9/2. Pit cavity varies from 5Y 8.5/4 to 5Y 8.5/6.

Skin:

*Thickness.*—Medium.

*Surface.*—Smooth.

*Down.*—Moderate amount, very short in length.

*Tendency to crack.*—None.

*Color.*—Ground color varies from 2.5Y 8.5/8 to 5Y 9/6. Overspread with 5R 4/10 to 7.5R 5/10 on approximately 70% of the fruit.

*Tenacity.*—Tenacious to flesh.

*Astringency.*—None.

Stone:

*Type.*—Clingstone.

*Size.*—Medium. Average length 26.3 mm. Average width 18.8 mm. Average depth 14.0 mm.

*Form.*—Obovoid.

*Base.*—Flat.

*Apex.*—Nearly rounded, slight point. Average length 0.3 mm.

*Surface.*—Very lightly pitted throughout, pit cavities vary from round to slightly elongated. One furrow on each side of suture.

*Sides.*—Vary from equal to unequal with one side extending further from suture plane.

*Ridges.*—Relatively small and smooth.

*Tendency to split.*—Very slight.

*Color.*— 5Y 9/2, when dry.

Kernal:

*Form.*—Ovate.

*Taste.*—Bitter.

*Viability.*—Non-viable, incomplete embryo.

*Size.*—Medium. Average length 15.3 mm. Average width 9.9 mm. Average depth 5.0 mm.

*Skin color.*— 5Y 8.5/2, when dry.

Use: Dessert. Market — local and long distance.

Keeping quality: Good, held firm in cold storage at 38° to 42° F. for 10 days without internal breakdown or appreciable loss of flavor.

Shipping quality: Good, minimal bruising of flesh or skin scarring during picking and packing trials.

Plant/fruit disease resistance susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. A new and distinct variety of peach tree, substantially as illustrated and described, characterized by its low winter chilling requirement, its large size, vigorous upright growth and being a regular and productive bearer of medium size, early maturing, white flesh, clingstone fruit with a mild, sweet, sub-acid flavor and excellent eating quality; the fruit is further characterized by having an attractive orange-red skin color and, in comparison to the low chilling variety 'Desertgold' Peach (non-patented), the fruit has a more attractive red skin color, firmer flesh and is approximately 27 days earlier in maturity.

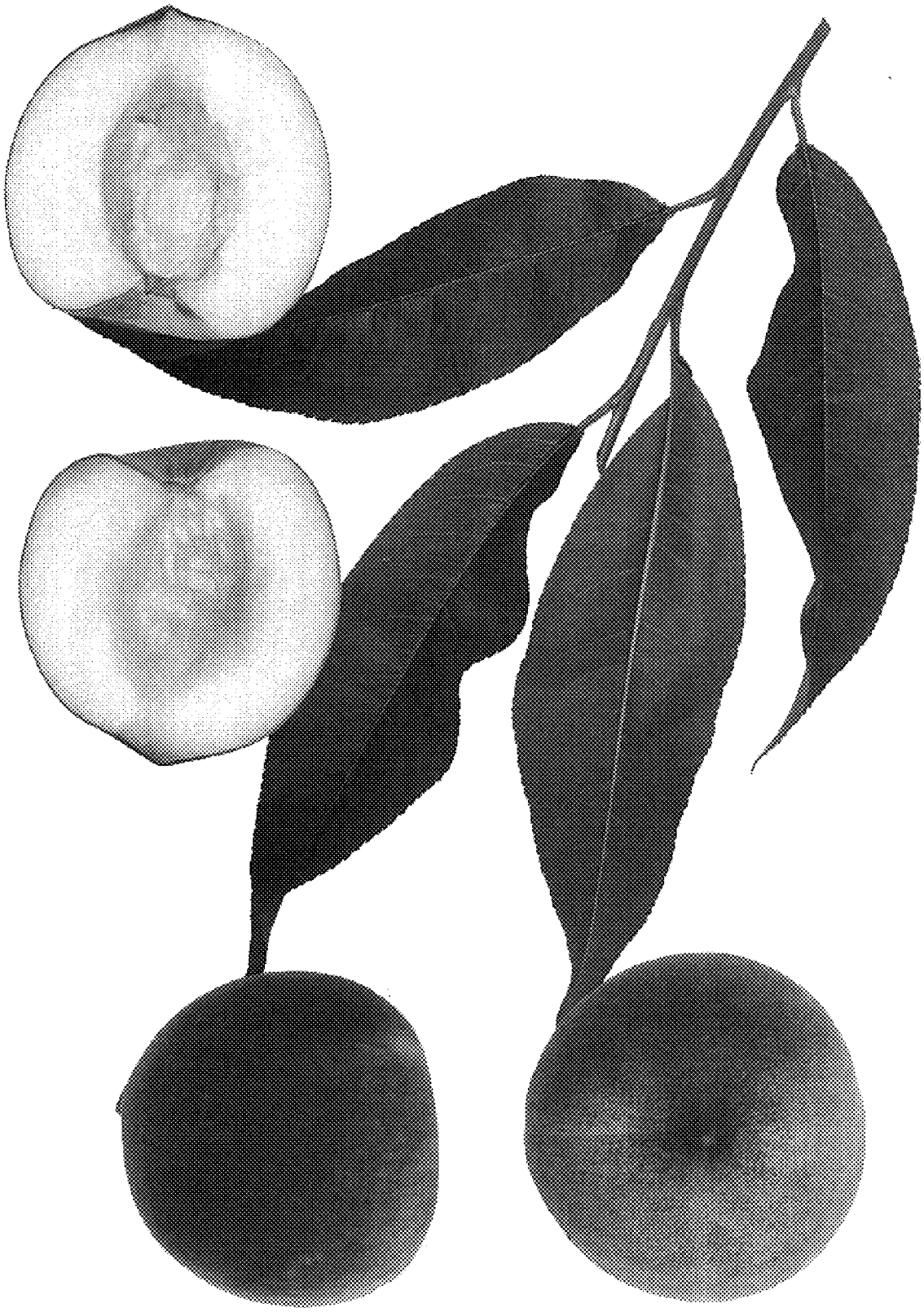

* * * * *